United States Patent [19]

Araya

[11] Patent Number: 5,677,534
[45] Date of Patent: Oct. 14, 1997

[54] APPARATUS FOR NON-DISPERSIVE INFRARED ANALYZER

[75] Inventor: Katsuhiko Araya, Uji, Japan

[73] Assignee: Shimadzu Corp., Kyoto, Japan

[21] Appl. No.: 648,486

[22] Filed: May 15, 1996

[30] Foreign Application Priority Data

May 29, 1995 [JP] Japan ............ 7-130820

[51] Int. Cl.⁶ ............ G01N 21/61
[52] U.S. Cl. ............ 250/345
[58] Field of Search ............ 250/345, 351

[56] References Cited

U.S. PATENT DOCUMENTS

| | | | |
|---|---|---|---|
| 2,555,327 | 6/1951 | Elliott | 250/345 |
| 3,454,760 | 7/1969 | Kowert et al. | 250/345 |
| 4,008,394 | 2/1977 | Risgin et al. | 250/345 |

FOREIGN PATENT DOCUMENTS

| | | | |
|---|---|---|---|
| 3504140 | 8/1986 | Germany | 250/351 |

Primary Examiner—Carolyn E. Fields
Attorney, Agent, or Firm—Nikaido Marmelstein Murray & Oram LLP

[57] ABSTRACT

An infrared light beam, emitted from an infrared light source 4, arrives periodically and alternatively at a sample cell 1a and reference cell 1b through a rotating chopper 2. The beam, which travels through the sample cell 1a and reference cell 1b, is detected as a sample signal and reference signal by a detector 5. The chopper 2 has apertures 2a and 2a. Since the aperture 2a, which faces the sample cell 1a, and the aperture 2b, which faces the reference cell 1b, are each formed in an arc shape having a central angle of about 90 degrees, the amount of time for which the infrared light beam is emitted and not emitted to the sample cell 1b and the reference cell 1a are all about equal. Therefore, the non-dispersive infrared analyzer can obtain about twice the amount of information about the concentration of the gas to be measured than a conventional apparatus per one chopper rotation.

5 Claims, 4 Drawing Sheets

APPARATUS FOR NON-DISPERSIVE INFRARED ANALYZER

BACKGROUND OF THE INVENTION (1) Field of the Invention

The present invention relates to non-dispersive infrared analyzer for continuously detecting the concentration of a preselected gas in a sample gas using an adsorption band of infrared light which is a characteristic of the preselected gas.

(2) Description of the Related Art

Non-dispersive infrared analyzers are now widely used for measuring gas concentration for various types of exhaust gases in order to monitor the exhaust for air pollution, and for measuring gas concentration in industrial processes, etc. One such non-dispersive infrared analyzer, as an example, is described in U.S. Pat. No. 4,355,233 by Warnke et al.

A prior art non-dispersive infrared analyzer is illustrated in FIGS. 4a–4b. In the FIG. 4a, an infrared light beam from an infrared light source 14 is output to a cylindrical sample cell 11a and cylindrical reference cell 11b. The emitted beam is periodically and alternatively output to the sample cell 11a and reference cell 11b by a rotating chopper 12 which is connected to a motor 13 by an axle 13a. The chopper 12 rotates at a constant speed, for example, one rotation per second(1 Hz), to interrupt the infrared light.

As shown in FIG. 4b, the rotating chopper 12 has a disc shape with a first aperture 12a and a second aperture 12b which are both in the form of an arc.

The first aperture 12a and the second aperture 12b are located opposite to the sample cell 11a and reference cell 11b, respectively. The central angles 12c of the arc shape of both apertures 12a, 12b are much less than 90 degrees such as 30 degrees.

The sample cell 11a and the reference cell 11b are periodically and alternatively exposed to the emitted beam in a time-sharing manner through the first aperture 12a and the second aperture 12b in the chopper 12 which continuously rotates.

A sample gas containing the gas to be measured is continuously streamed through the sample cell 11a. A reference gas such as N2 gas which does not absorb infrared light energy fills the reference cell 11b.

The infrared light beam, after traveling through the sample cell 11a or the reference cell 11b, arrives at a chamber 15a in a detector 15. The chamber 15a, 15b in the detector 15 are filled with the same kind of gas as that to be measured, and are separated by a diaphragm 15c. The diaphragm 15c is a very thin sheet of a conductive material, such as titanium foil, which serves as a variable plate of a capacitor. Disposed next to diaphragm 15c is an electrode 15d which serves as a fixed plate of the capacitor.

Infrared energy within the absorption band, characteristic of the gas to be measured, is absorbed by the same gas in the chamber 15a. Thus, the gas in the chamber 15a becomes heated to a greater extent than that in the chamber 15b. The unequal heating in the chambers 15a and 15b will produce a pressure difference, causing deflection of diaphragm 15c which, in turn, will vary the capacitance established between electrode 15d and diaphragm 15c.

Therefore, the detector 15 can output the signal corresponding to the inside pressure difference caused by absorbing the infrared light.

The output signal obtained from the detector 15 after one rotation of the chopper 12 is illustrated in FIG. 5. Since the infrared light energy is not absorbed by the gas in the reference cell 11b when the beam travels through the reference cell 11b, all the infrared energy within the absorption band, which is characteristic of the gas to be measured, is absorbed by the same gas in the detector 15. Therefore, a reference signal obtained from the detector 15 shows a maximum value.

On the other hand, when the beam travels through the sample cell 11a, since the infrared energy is absorbed by the gas to be measured in the sample cell 11a, the energy absorbed by the same gas in the detector 15 is reduced by the amount of energy absorbed in sample cell 11a. Therefore, a sample signal output from the detector 15 shows a value which is reduced by a value corresponding to the amount of gas to be measured in the sample cell 11a.

A signal processor 16 integrates the oblique line parts in FIG. 5 of the reference signal and the sample signal, respectively. Repeating these operations over many rotations of the chopper 12, the processor 16 averages the integrated value obtained over many rotations of the chopper 12, respectively, to reduce noise. Then, the signal processor 16 produce a normalized intensity ratio by calculating the ratio of the averaged value for the sample signal to that for the reference signal in order to eliminate an effect caused by the fluctuation of the emitted beam intensity and/or the fluctuation of the sensitivity of the detector 15.

Then, the signal processor 16 produces the concentration of the gas to be measured in the sample cell 11a from the normalized intensity ratio on the basis of a calibration curve prepared in advance.

As mentioned above, in the prior art non-dispersive infrared analyzer, as the central angle 12c of the apertures 12a, 12b in the chopper 12 is much less than 90 degree, as shown in FIG. 4b, only the oblique line part in FIG. 5 formed by the reference signal and sample signal can be used for calculating the gas concentration. Therefore, when the reference signal and the sample signal are integrated over many rotations of the chopper 12 to reduce the detection noise, it takes a long time to measure the concentration because only the oblique line parts in FIG. 5 are used.

Especially, in case the concentration variation of the gas to be measured in the sample gas is relatively fast, it become impossible to measure the gas concentration precisely because all information obtained from the reference signal and the sample signal is not used.

SUMMARY OF THE INVENTION

It is therefore an object of the present invention to use all information obtained from the reference signal and the sample signal for calculating the gas concentration.

It is another object of the present invention to have high efficient data acquisition.

It is a further object of the present invention to shorten the amount of measurement time.

It is a further object of the present invention to measure the gas concentration more precisely even when the concentration variation of the gas to be measured in the sample gas is relatively fast.

The foregoing objects are achieved and the foregoing deficiencies are overcome by the present invention.

BRIEF DESCRIPTION OF THE DRAWINGS

The above and other objects and attendant advantages of the preset invention will become readily apparent by reference to the following detailed description when considered in conjunction with the accompanying drawing, wherein.

DESCRIPTION OF THE PREFERRED EMBODIMENT

Figure 1A:
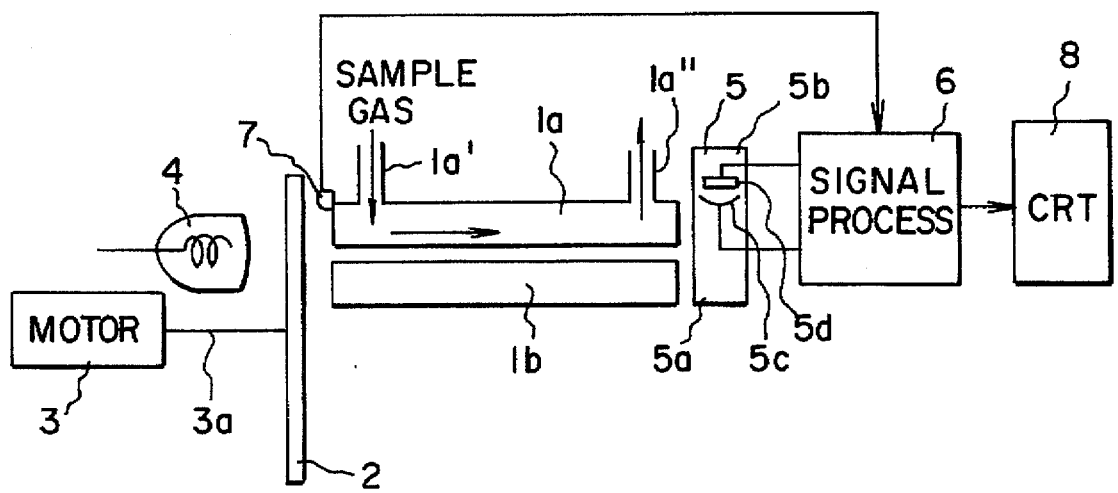
FIGS. 1a–1b illustrate one embodiment of a non-dispersive infrared analyzer and chopper constructed in accordance with the present invention.
Figure 1B:
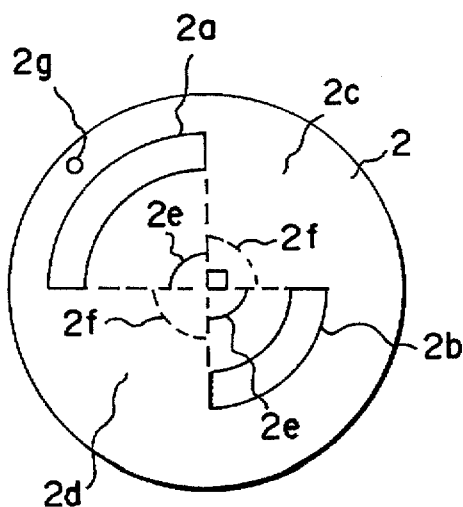

In FIG. 1, FIG. 1a illustrates one embodiment of a non-dispersive infrared analyzer constructed in accordance with the present invention, and FIG. 1b illustrates one embodiment of a chopper used for the non-dispersive infrared analyzer constructed in accordance with the present invention.

In FIG. 1a, the infrared light beam from an infrared light source 4 is output to a cylindrical sample cell 1a and a cylindrical reference cell 1b.

A rotation chopper 2 is placed between the light source 4 and the cells 1a, 1b. The chopper 2 is connected to a motor 3 by a axle 3a and rotates to interrupt the beam by continuous rotation, for example, one rotation per one second(1 Hz). As shown in FIG. 1b, the rotating chopper 2 has a disc shape with a first aperture 2a and a second aperture 2b which are each in the form of an arc and pass infrared light. The first aperture 2a and the second aperture 2b are formed in the chopper 2 opposite the beam entrance to the sample cell 1a and the reference cell 1b, respectively. The aperture 2a is placed on the opposite side of the aperture 2b. Other parts of chopper 2 include shielding parts 2c, 2d operate to block the beam from passing to the cells 1a, 1b. The central angles 2e of the arc shape of both apertures 2a, 2b and an angle 2f of the shielding parts 2c, 2d are all up approximately 90 degrees.

A small aperture 2g, which passes infrared light, is formed near the aperture 2a in the chopper 2. An optical infrared sensor 7, such as a photodiode, is placed at a position facing the orbit of the small aperture 2g. The sensor 7 senses when the first aperture 2a passes over the sample cell 1a. The optical light sensor 7 feeds the position signal to the signal processor 6, which determines whether the signal from the detector 5 belongs to the sample signal generated by the beam traveling through the sample cell 1a or the reference signal 1b generated by the beam traveling through reference cell 1b.

The sample cell 1a and the reference cell 1b are periodically and alternatively exposed to the emitted beam by the rotating chopper 2 which rotates at a constant speed. The amount of exposure time of the emitted beam to both cells 1a, 1b becomes approximately equal to the amount of no exposure time to both cells 1a, 1b.

A detector 5, which can be a pneumatic detector, has detector chambers 5a and 5b which are generally filled with the same kind of gas as that to be measured. The chambers 5a, 5b are separated by a diaphragm 5c. The diaphragm 5c is a very thin sheet of a conductive material such as titanium foil which serves as a variable plate of a capacitor. Disposed next to the diaphragm 5c is an electrode 5d which serves as a fixed plate of the capacitor.

Infrared energy within the absorption band, which is characteristic of the gas to be measured, will be absorbed by the same gas in the chamber 5a. Thus, the gas in chamber 5a becomes heated to a greater extent than that in the chamber 5b. The unequal heating in the chambers 5a and 5b will produce a pressure difference, causing deflection of diaphragm 5c which, in turn, will vary the capacitance established between electrode 5d and diaphragm 5c.

Therefore, the detector 5 outputs a signal correspond to the inside pressure change caused by absorbing the infrared light.

The detector 5 is positioned such that the infrared light beam, which travels through the sample cell 1a or the reference cell 1b, only enters chamber 5a and does not enter chamber 5b.

Figure 3A:
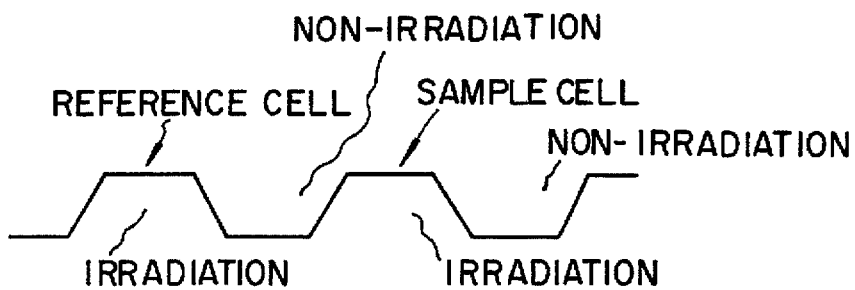
FIGS. 3a–3e illustrate one embodiment of time charts of a sample signal and a reference signal obtained by the non-dispersive infrared analyzer constructed in accordance with the present invention.
Figure 3B:
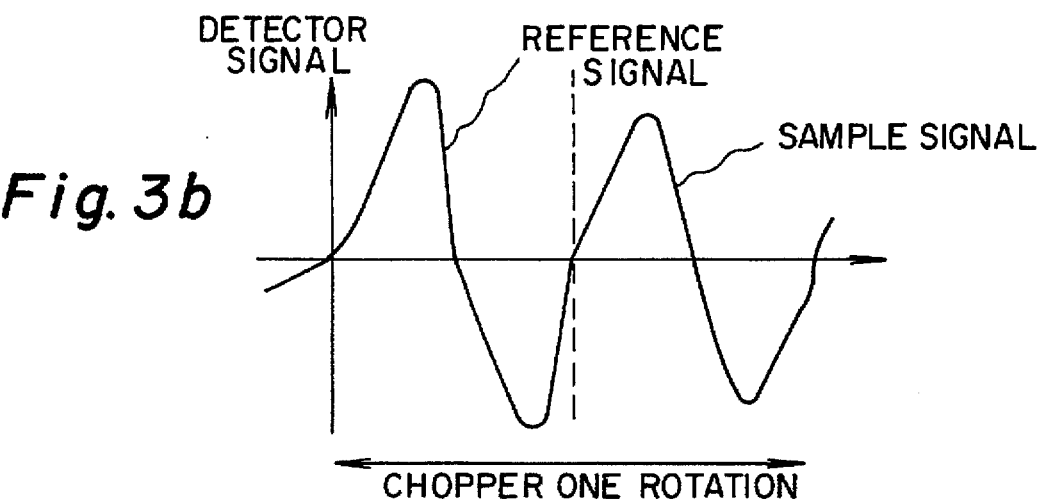

FIG. 3b shows a detector signal obtained from the detector 5. Since the infrared light beam is not absorbed in the reference cell 1b, all the infrared energy within the absorption band, which is characteristic of the gas to be measured, is absorbed in the detector 5 so that the reference signal output from the detector 5 becomes a maximum value.

On the other hand, since the infrared energy within the absorption band, which is characteristic of the gas to be measured, is absorbed by the gas to be measured in the sample cell 1a, a sample signal output from the detector 15 when detecting a beam passing through the sample cell 1a becomes a value which is reduced by a value corresponding to the amount of the gas to be measured in the sample cell 1a.

Figure 2:
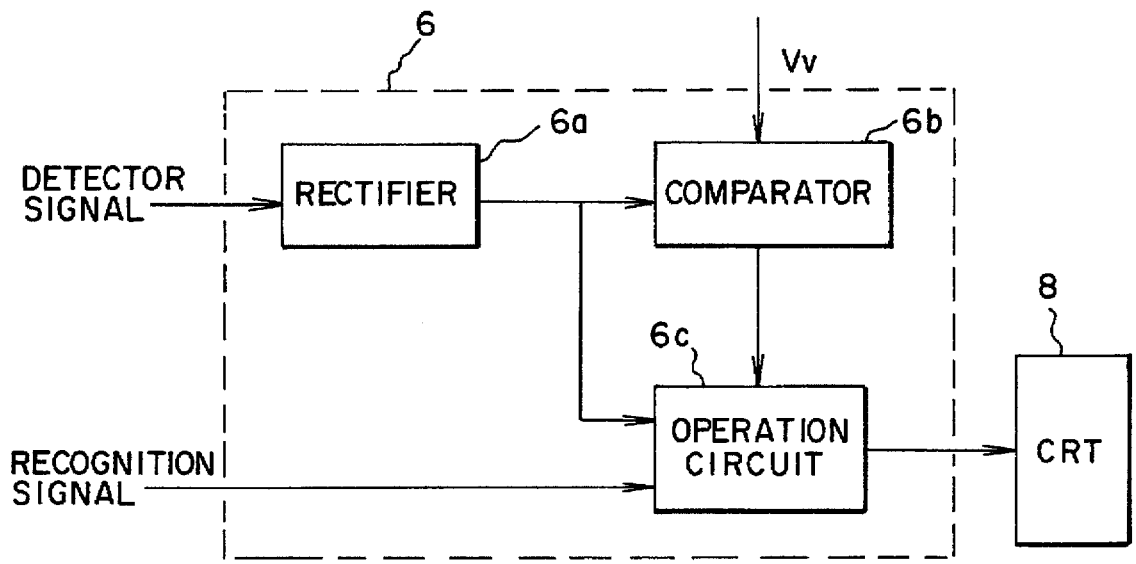
FIG. 2 illustrates one embodiment of a signal processor constructed in accordance with the present invention.
Figure 5:
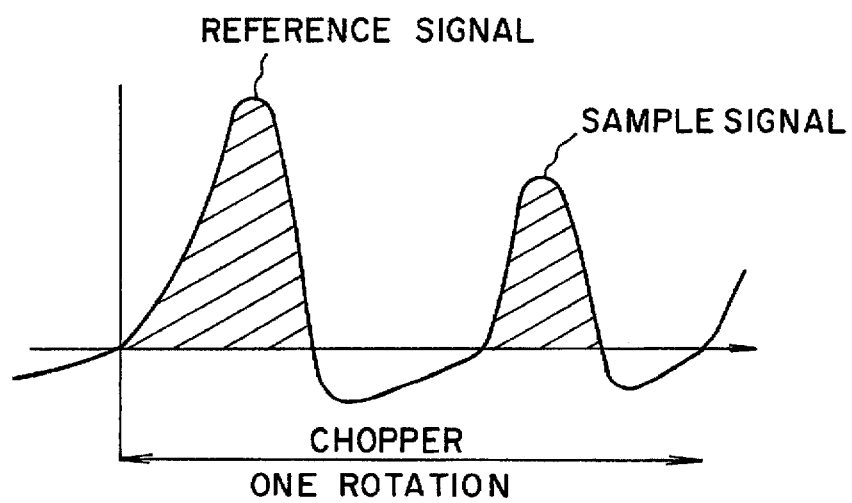
FIG. 5 illustrates a time chart of a sample signal and a reference signal obtained from the detector of the prior art non-dispersive infrared analyzer.
Figure 3C:
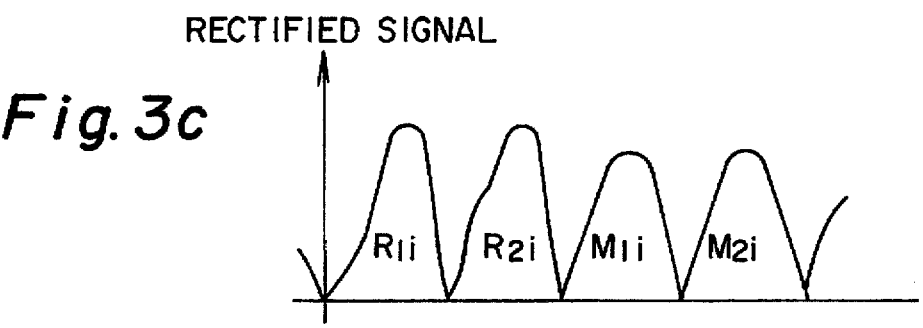

As shown in FIG. 2, a signal processor 6 consists of a full-wave rectifier 6a, a comparator 6b and an operation circuit 6c. As shown in FIG. 3c, the full-wave rectifier 6a rectifies the detector signal shown in FIG. 3b from the detector 5.

Figure 3D:
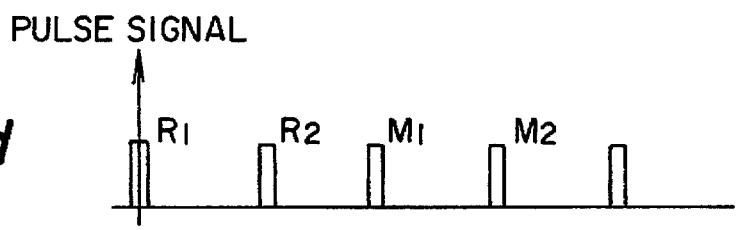
Figure 3E:
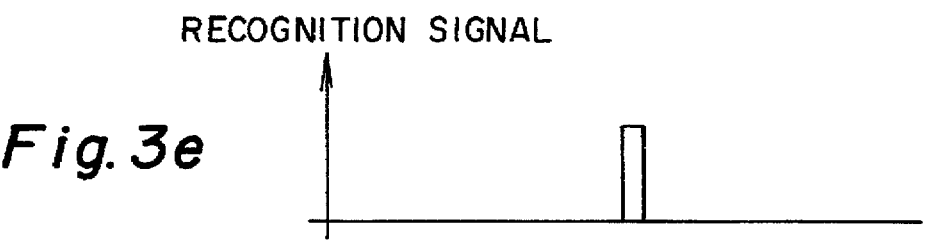
Figure 4A:
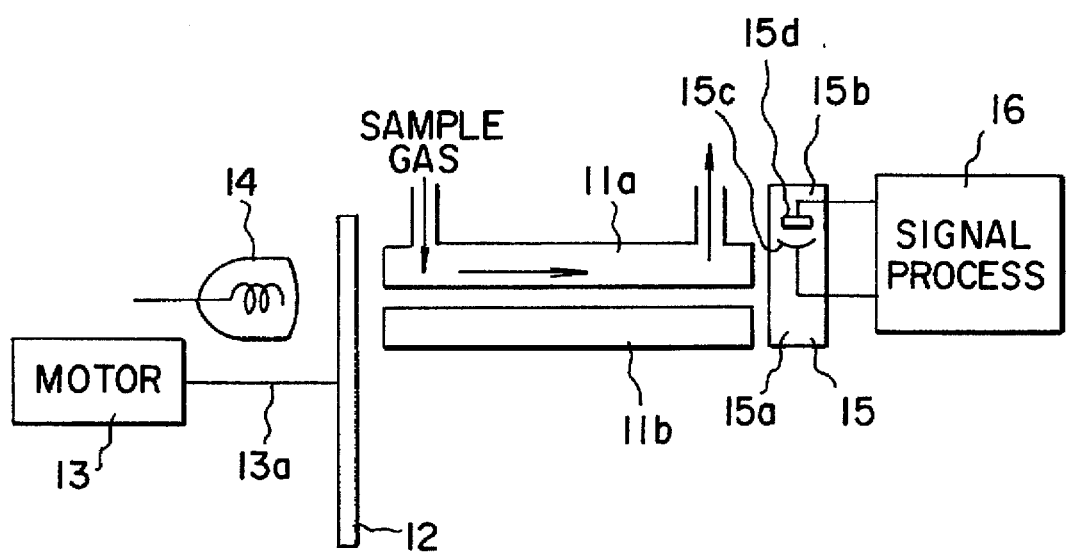
FIGS. 4a–4b illustrate a prior art non-dispersive infrared analyzer and chopper.
Figure 4B:
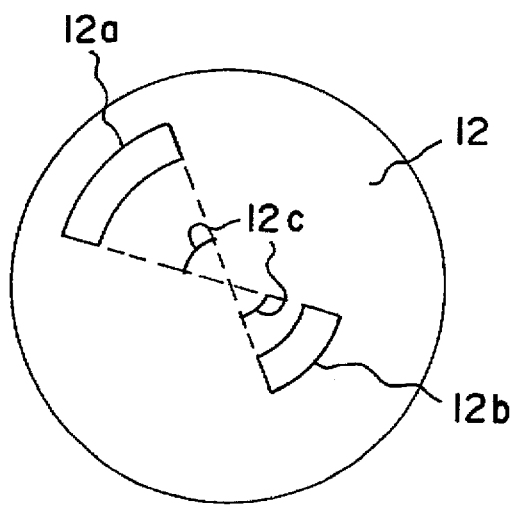

The comparator 6b compares the rectified signal shown in FIG. 3c with the reference voltage which is a smaller voltage, for example, 10% voltage of the voltage corresponding to the maximum value. The comparator 6b outputs the pulse signal as the leading edge of the reference signal and sample signal as shown in FIG. 3d.

The operation circuit 6c starts integrating the rectified signal from the full-wave rectifier 6a when the trailing edge of the pulse signal from the comparator 6b is recognized, and stops integrating when the leading edge of the pulse signal from the comparator 6b is recognized, then stores the integrated value.

The operation circuit 6c recognizes the two integral values M1i, M2i, which are obtained after the recognition signal e from optical light sensor 7 is input, as first and second measurements. The operation circuit 6c recognizes two integrated values R1i, R2i, which are obtained before the recognition signal e from the optical light sensor 7 is input, as first and second reference values. Then the operational circuit 6c calculates the normalized intensity ratio r of the sample signal by the following equation:

$$r = (\Sigma M1i + \Sigma M2i)/(\Sigma R1i + \Sigma R2i)$$

wherein "i" indicates a data number of the plural data obtained by making the chopper 2 rotate several times, and "Σ" indicates the summation of the data obtained by every rotation of the chopper 2.

Furthermore, the operational circuit 6c converts the normalized intensity ratio r into the concentration of the gas to be measured by using a calibration curve which is prepared in advance.

The concentration of the gas to be measured is displayed on a CRT 8.

The operation of the present invention is as follows:

The infrared light beam from the infrared light source 4 is periodically and alternatively output to the sample cell 1a and the reference cell 1b by making chopper 2 rotate.

The infrared beam, which travels through the sample cell 1a and reference cell 1b, is detected by the detector 5 as the sample signal 1a and the reference signal, respectively, as shown in FIG. 3b. Since the aperture 2a facing with the sample cell 1a and the aperture 2b facing with the reference cell 1b are each formed in an arc shape having a central angle of about 90 degrees in the chopper 2 as shown in FIG. 1b, each amount of time for which the infrared light beam is emitted and not emitted to the sample cell 1a, and to the reference cell 1b are all about equal.

Therefore, the shape of the sample signal detected by the detector 5 through emission or unemission of the infrared light beam is approximately symmetrical with respect to the time-axis as shown in FIG. 3b, and the reference signal detected by the detector 5 is the same as that of the sample signal.

After these signals are full-wave rectified by the full-wave rectifier 6a, not only the signal obtained by infrared emission but also the signal obtained by infrared unemission are integrated and used for measuring the concentration of the gas to be measured in the operation circuit 6c.

Therefore, the non-dispersive infrared analyzer of the present invention can obtain about twice the amount of information about the concentration of the gas to be measured than a conventional apparatus per one chopper rotation.

Thus, in the present invention, it takes half the amount of time to measure the concentration of the gas as in the conventional.

Therefore, the present invention enables high-precise measurement of the concentration of the gas to be measured even when the concentration of the gas to be measured varies relatively fast.

Although the embodiments of the present invention have been described in detail, it will be understood that the present invention is not limited to the above-described embodiments, and various modifications in design may be made without departing from the spirit and scope of the invention defined in the claims.

What is claimed:

1. A non-dispersive infrared analyzer, comprising:

an infrared light source for emitting an infrared light beam;

a reference cell having an infrared light passage and being filled with a reference gas;

a sample cell configured to have a gas flow therethrough, said sample cell having an infrared light passage through which both a sample gas, containing a gas to be measured, and said infrared light beam, emitted from said infrared source, pass;

an interrupter for interrupting said infrared light beam, said interrupter performing first irradiation of the beam for said reference cell, first non-irradiation of the beam for both the sample and reference cells, second irradiation of the beam for said sample cell, and second non-irradiation of the beam for both the sample and reference cells, one after another so that an amount of first radiation and first non-irradiation time are approximately equal and an amount of second irradiation and second non-irradiation time are approximately equal;

discrimination means for discriminating irradiation or non-irradiation of said infrared light beam for said reference cell or said sample cell and for generating a discrimination signal;

a detector is located so that said infrared light beam, which traveled through one of said reference cell and said sample cell, enters thereinto, and said detector sensing the infrared energy at said infrared light wavelength corresponding to an absorption band of gas to be measured;

a processing means, coupled to said detector and said discrimination means, for receiving the discrimination signal from the discrimination means and an electrical signal from said detector, said processing means for integrating the electrical signal obtained from said detector by irradiation and non-irradiation of the infrared beam for the reference cell and the electrical signal obtained from said detector by irradiation and non-irradiation of the infrared beam for the sample cell, respectively, said processing means for producing a normalized intensity value by calculating a ratio of both integrated values and for calculating a concentration of the gas to be measured in said sample cell.

2. A non-dispersive infrared analyzer as recited in claim 1, wherein said interrupter being a chopper located between the infrared light source and said both sample and reference cells, wherein the chopper has a disc shape with a first aperture and a second aperture which passes infrared light, the first aperture being formed in an arc shape at a place facing said sample cell, and the second aperture being formed in an arc shape at a place facing said reference cell, wherein central angles of the arc shape of both first and second apertures and a central angle of a shielding part, which is a part except an aperture part of the chopper, are all approximately 90 degrees.

3. A non-dispersive infrared analyzer as recited in claim 1, wherein said discrimination means being a) a discrimination aperture formed at a position near the first or second aperture on the chopper and b) a optical sensor placed in a light path passing through the discrimination aperture.

4. A non-dispersive infrared analyzer as recited in claim 1, wherein said detector comprises a pneumatic detector having a chamber therein, and wherein the chamber being filled with the gas to be measured.

5. A non-dispersive infrared analyzer as recited in claim 1, wherein said processing means includes a full-wave rectifier for full-wave rectifying the electrical signal obtained from said detector, a comparator for detecting a leading edge and trailing edge of a rectified signal by comparing a full-wave rectified signal with a reference voltage, and an operation means for integrating the rectified signal obtained by the infrared light traveling through said reference cell and that obtained by the infrared light traveling through said sample cell, respectively, said operation means for producing a normalized intensity ratio by calculating a ratio of both integrated values and calculating a concentration of the gas to be measured in said sample cell by using a calibration curve prepared in advance.

* * * * *